(12) United States Patent
Folan et al.

(10) Patent No.: US 12,121,647 B2
(45) Date of Patent: Oct. 22, 2024

(54) ENDOLUMINAL SEALING DEVICES AND RELATED METHODS OF USE

(71) Applicant: Boston Scientific Scimed, Inc., Maple Grove, MN (US)

(72) Inventors: Martyn Folan, Loughrea (IE); Matthew Montague, Oranmore (IE); Michael Walsh, Rosscahill (IE); Louis McNern, Killybegs (IE); John T. Favreau, Spencer, MA (US); Shawn Ryan, Littleton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 215 days.

(21) Appl. No.: 17/183,542

(22) Filed: Feb. 24, 2021

(65) Prior Publication Data

US 2021/0260259 A1 Aug. 26, 2021

Related U.S. Application Data

(60) Provisional application No. 62/981,733, filed on Feb. 26, 2020.

(51) Int. Cl.
*A61M 1/00* (2006.01)
*A61B 17/00* (2006.01)
(Continued)

(52) U.S. Cl.
CPC ............ *A61M 1/90* (2021.05); *A61B 17/0057* (2013.01); *A61F 2/04* (2013.01);
(Continued)

(58) Field of Classification Search
CPC ............ A61M 1/90; A61M 2210/1042; A61B 17/0057; A61B 2017/0061;
(Continued)

(56) References Cited

U.S. PATENT DOCUMENTS 10,058,413 B2 8/2018 Heiss
10,456,511 B2 10/2019 Kleiner
(Continued)

FOREIGN PATENT DOCUMENTS

DE 102014005679 A1 10/2015
WO 2014044400 A1 3/2014
(Continued)

OTHER PUBLICATIONS

International Search Report and Written Opinion in International Application No. PCT/US2021/019332, mailed Aug. 2, 2021 (18 pages).

*Primary Examiner* — Leslie A Lopez
*Assistant Examiner* — Timothy L Flynn
(74) *Attorney, Agent, or Firm* — Bookoff McAndrews, PLLC

(57) ABSTRACT

A medical system includes a porous body positioned at a target site within a subject, a tube including a wall defining a tube lumen, where the tube is connected to the porous body at a first end of the tube, and a sealing device to seal the target site from a body lumen. When the sealing device seals the target site from the body lumen, the tube extends from the target site into the body lumen.

19 Claims, 7 Drawing Sheets

(51) Int. Cl.
   *A61F 2/00*    (2006.01)
   *A61F 2/04*    (2013.01)
(52) U.S. Cl.
   CPC .............. *A61B 2017/0061* (2013.01); *A61B 2017/00632* (2013.01); *A61F 2002/0081* (2013.01); *A61F 2002/045* (2013.01); *A61F 2250/0059* (2013.01); *A61M 2210/1042* (2013.01)
(58) Field of Classification Search
   CPC ............. A61B 2017/00632; A61F 2/04; A61F 2002/0081; A61F 2002/045; A61F 2250/0059
   See application file for complete search history.

(56) References Cited

U.S. PATENT DOCUMENTS

| | | | |
|---|---|---|---|
| 10,722,622 B2* | 7/2020 | Loske | ................... A61B 17/42 |
| 10,779,928 B2 | 9/2020 | Heiss | |
| 2008/0033528 A1 | 2/2008 | Satasiya et al. | |
| 2014/0031773 A1* | 1/2014 | Mikkaichi | ........... A61M 3/0279 604/319 |
| 2015/0105850 A1* | 4/2015 | Shahriari | .................. A61F 2/90 29/446 |
| 2015/0250979 A1 | 9/2015 | Loske | |
| 2016/0361477 A1 | 12/2016 | Loske | |
| 2016/0361477 A1 | 12/2016 | Loske et al. | |
| 2016/0367352 A1* | 12/2016 | Heiss | ......................... A61F 2/04 |
| 2017/0150971 A1* | 6/2017 | Hines | ............... A61B 17/12172 |
| 2019/0365521 A1 | 12/2019 | Burke et al. | |
| 2020/0138422 A1* | 5/2020 | Hebert | ................... B29D 23/00 |
| 2020/0214861 A1* | 7/2020 | McWeeney | ............. A61F 2/966 |
| 2020/0276056 A1 | 9/2020 | Leeds | |
| 2021/0228786 A1* | 7/2021 | Perry | ..................... A61M 1/73 |

FOREIGN PATENT DOCUMENTS

| | | |
|---|---|---|
| WO | 2014197743 A1 | 12/2014 |
| WO | 2015086037 A1 | 6/2015 |
| WO | 2019059893 A1 | 3/2019 |

* cited by examiner

ENDOLUMINAL SEALING DEVICES AND RELATED METHODS OF USE

CROSS-REFERENCE TO RELATED APPLICATIONS

This application claims the benefit of priority from U.S. Provisional Application No. 62/981,733, filed on Feb. 26, 2020, which is incorporated by reference herein in its entirety.

TECHNICAL FIELD

This disclosure relates to minimally invasive (e.g., endoscopic and/or laparoscopic) medical devices and related methods of use. In embodiments, the disclosure relates to one or more devices for sealing perforations, leaks, or wounds in the gastrointestinal tract, devices for advancing these sealing devices, and related methods of use, among other aspects.

BACKGROUND

Endoscopic and open surgical procedures of the gastrointestinal (GI) tract include, for example, colonic resection, bariatric surgery, esophagectomy, gastric bypass, and sleeve gastrectomy, among others. These procedures may result in perforation, post-surgical leaks, or other wounds of the tract. Limited treatment options exist for managing such wounds, which have significant morbidity and mortality rates. Options include surgical re-operation and endoscopic placement of a stent or clips. Surgery is relatively invasive and also has high morbidity and mortality rates. Endoscopic stent placement is a less invasive option. The placed stent, however, can migrate from the intended location and/or wall off infection at the target site, inhibiting drainage.

SUMMARY OF THE DISCLOSURE

According to an aspect, a medical system includes a porous body configured to be positioned at a target site within a subject, a tube including a wall defining a tube lumen, wherein the tube is connected to the porous body at a first end of the tube, and a sealing device configured to seal the target site from a body lumen, wherein, when the sealing device seals the target site from the body lumen, the tube is configured to extend from the target site into the body lumen.

The sealing device may be a stent, and the stent may be configured to contact (1) a sidewall of the body lumen and (2) the tube, when the tube and the stent are implanted.

The stent may include a wall defining a stent lumen, and an attachment device may extend from the wall into the stent lumen.

The wall of the stent may define a channel extending along an outer surface of the stent.

The wall of the stent may include a radially-outward-facing concave surface and a radially-inward-facing convex surface along a length of the channel.

The channel may be configured to be aligned with the tube when the tube and the stent are implanted, and the tube may be configured to extend within the channel to seal the target site from the body lumen.

The channel may include a sloped surface angled relative to a central longitudinal axis of the stent lumen, and the sloped surface may be configured to accommodate the tube.

The sealing device may be a valve defining a valve lumen therethrough, wherein the valve may be configured to be positioned within an opening in a wall defining the body lumen between the target site and the body lumen, and wherein the tube may be configured to extend from the target site, through the valve lumen, and into the body lumen.

The valve may have (1) a closed configuration in which the valve contacts the tube, and (2) an open configuration in which the valve does not contact the tube.

The valve may be configured so that a size of the valve lumen varies due to a peristaltic action of the wall defining the body lumen.

An outer surface of the valve may be U-shaped.

A fluid from the target site may be configured to be expelled from the target site via the tube lumen and the valve lumen.

The first end of the tube may include a plurality of branches embedded in the sponge.

The tube may include a plurality of corrugations, and wherein the tube may be configured to bend via the plurality of corrugations.

The tube may include a plurality of one-way valves, wherein the plurality of one-way valves may be configured to allow fluid to pass from the target site to the body lumen, and may inhibit fluid from passing from the body lumen to the target site.

According to another aspect, a medical device includes a porous body and a tube, the tube including a tube lumen extending from a first end of the tube to a second end of the tube and connected to the porous body at the first end of the tube, wherein the tube includes at least one one-way valve configured to pass fluid from the first end of the tube to the second end of the tube and inhibit fluid from passing from the second end of the tube to the first end of the tube, and wherein the tube lumen is fluidly connected to the porous body at the first end of the tube.

The first end of the tube may include a plurality of branches embedded with the porous body, wherein the tube lumen may extend through each branch of the plurality of branches, and each branch of the plurality of branches may include an opening fluidly connecting the tube lumen with the porous body.

The tube may include a plurality of corrugations, and wherein the tube may be configured to bend via the plurality of corrugations.

According to yet another aspect, a method of removing fluid from a target site adjacent a gastrointestinal tract comprises deploying a porous body at the target site, wherein a tube extends from the porous body into the gastrointestinal tract, and deploying a stent within the gastrointestinal tract to seal the target site from the gastrointestinal tract.

The method may further comprise moving an end of the stent into the stent lumen, removing the porous body from the gastrointestinal tract, deploying a second porous body at the target site, and moving the end of the stent from the stent lumen to seal the target site from the gastrointestinal tract.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Figure 1A:
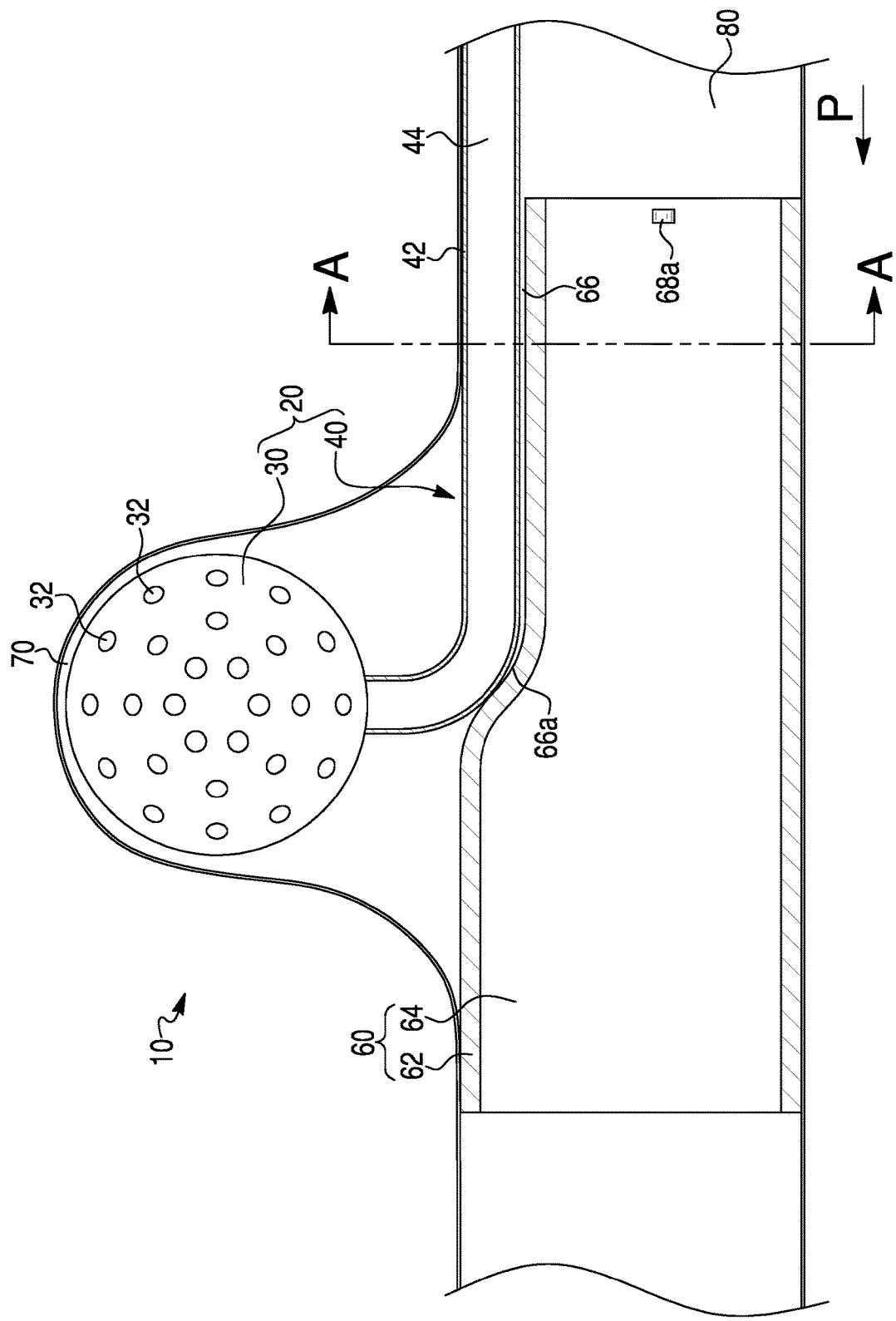
FIG. 1A is a cross-section of an endoluminal vacuum therapy (EVAC) system according to an embodiment.

For ease of description, portions of the disclosed devices and/or their components are referred to as proximal and distal portions. It should be noted that the term "proximal" is intended to refer to portions closer to a user of the devices, and the term "distal" is used herein to refer to portions further away from the user. Similarly, "extends distally" indicates that a component extends in a distal direction, and "extends proximally" indicates that a component extends in a proximal direction. Further, as used herein, the terms "about," "approximately," and "substantially" indicate a range of values within +/−10% of a stated or implied value. Terms that indicate the geometric shape of a component/surface refer to exact and approximate shapes. This disclosure may be understood with reference to the following description and the appended drawings, wherein like elements are referred to with the same reference numerals.

Endoluminal vacuum therapy (EVAC) has been proposed. In EVAC, negative pressure is delivered to the wound site in the GI tract, for example through a nasogastric tube having a sponge at its terminal end. The sponge is placed endoscopically into the perforation, leak, or other wound. Negative pressure then is applied. Devices and systems suited for EVAC are limited, however.

Embodiments of this disclosure include devices, systems, and methods for endoluminal vacuum therapy (EVAC). In examples, EVAC includes endoluminal placement of a sponge or other like material into the wound (e.g., target) site, including a perforation, a leak, a cyst, an anastomosis, etc. Placement of the material may be via a catheter, scope (endoscope, bronchoscope, colonoscope, duodenoscope, gastroscope, etc.), tube, or sheath, inserted into the GI tract via a natural orifice. The orifice can be, for example, the nose, mouth, or anus, and the placement can be in any portion of the GI tract, including the esophagus, stomach, duodenum, large intestine, or small intestine. Placement of the material also can be in other organs reachable via the GI tract.

FIG. 1A shows an EVAC system 10 in accordance with an example of this disclosure. System 10 may be inserted into a patient, e.g., at a target site 70 in a GI tract 80, for treatment of a chronic wound. As discussed herein, however, the location of system 10 in the body is not limited. System 10 generally includes an EVAC device 20 and a stent 60. While examples refer to GI tract 80, system 10 may be used in any internal body lumen.

EVAC device 20 may include a sponge 30 (or other mesh-like material or porous body) and a vacuum tube 40. Sponge 30 may be attached to a distal end of vacuum tube 40. Sponge 30 may include openings 32 on an outer surface thereof. Openings 32 may be any hole or pore which provides access to interconnecting channels and pores (not shown) throughout sponge 30 (for ease of reference, only openings 32 are shown). Openings 32 may have different sizes and/or shapes, and the size and the shape of openings 32 may be selected based on a location of treatment within the body. Fluid and/or other materials may be removed from target site 70. For ease of understanding, fluid will include any fluid, materials, or other debris contained within and/or removed from target site 70.

Sponge 30 is illustrated as having a spherical shape, but may be any shape, including a cylinder, cuboid, irregular, or the like. As will be discussed herein, sponge 30 may be compressed into a lower profile during insertion to a target site and may expand during deployment at the target site. Sponge 30 may initially have a first shape and size and may be trimmed during a medical procedure using, e.g., medical scissors or the like, to change the size and/or the shape of sponge 30 depending on the size and the shape of target site 70.

In embodiments of this disclosure, the sponge may be any suitable biocompatible material that may absorb liquids and/or permit liquid to pass therethrough via negative pressure. The material may be flexible, compressible, porous, hydrophilic, sterile, and/or disposable. The sponge material may be an open-cell foam. Suitable materials include polyurethanes, esters, ethers, composite materials, and any medical-grade material.

With continued reference to FIG. 1A, tube 40 may be a nasogastric tube includes an outer wall 42 defining one or more lumens 44. Lumen 44 includes an opening at a distal end of tube 40, and may include a single opening at the distal end. Alternatively, tube 40 that may contain one or more branches (see, e.g., branches 40a' in FIG. 3) at an end of tube 40 within sponge 30. Outer wall 42 may include a plurality of holes (not shown) around a circumference of the distal end of vacuum tube 40 and in fluid communication with lumen 44. These holes may increase the flow of fluid into lumen 44. The distal end of vacuum tube 40 may be attached to sponge 30 via sutures, an adhesive, or the like. In one example, sponge 30 may be cut to expose an interior of sponge 30 by, e.g., cutting sponge 30 into two halves of approximately equal size. Channels corresponding to the approximate shape and the approximate size of the distal end of tube 40 may be formed in each half of sponge 30. Tube 40 may be placed and/or attached within the channels of sponge 30, and the halves of sponge 30 may be recombined using an adhesive, sutures, or the like. This may provide additional structural support between sponge 30 and tube 40 and/or may allow sponge 30 to be formed around tube 40. For example, in the instance that tube 40 is an irregular shape and/or if tube 40 includes braches 40a', sponge 30 may be formed around tube 40. Alternatively, sponge 30 may be formed around the distal end of tube 40 via electrospinning, three-dimensional (3D) printing, or the like.

When placed in the body, the proximal end of tube 40 may extend proximally, i.e., in a direction opposite the direction indicated by arrow P in FIG. 1A, which may be a direction towards the insertion orifice. Arrow P indicates a direction of peristaltic action by GI tract 80, which will be described in greater detail below. The extension direction of the proximal end of tube 40 allows fluids to flow out of target site 70 and toward the insertion orifice via, e.g., a suction device attached to the proximal end of tube 40. Tube 40 may bend to allow tube 40 to extend in the proper direction in GI tract 80. For example, a diameter or thickness of outer wall 42 of tube 40 may be reduced and/or a different material may be used to assist in bending tube 40.

Figure 1B:
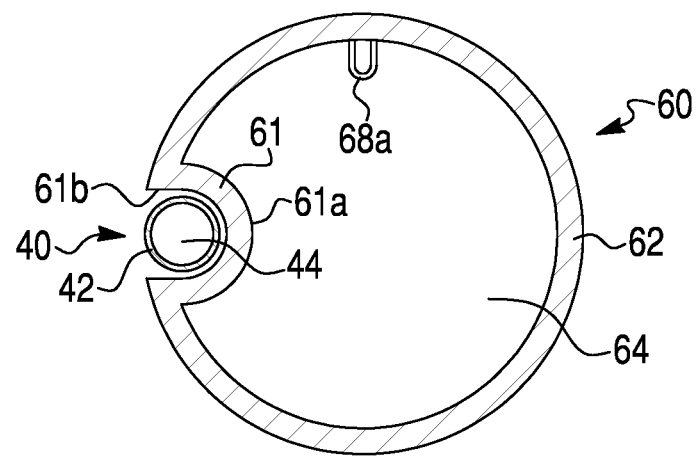
FIG. 1B is a cross-section of the EVAC system of FIG. 1A along the line A-A, according to an embodiment

With continued reference to FIG. 1A, stent 60 may include an outer wall 62 defining a lumen 64. Stent 60 may create a seal between target site 70 and GI tract 80. This seal may prevent fluid from entering target site 70 from GI tract 80 while allowing fluid and nutrients to pass through lumen 64 of stent 60. The fluid and nutrients may be taken up or absorbed by GI tract 80 in the normal course of the body's absorption of these materials. Stent 60 may include a channel 66 extending from a proximal end of stent 60 in a distal direction, and channel 66 may terminate proximally of the distal end of stent 60. FIG. 1B is a cross-sectional view of system 10 taken along the line A-A of FIG. 1A. Channel 66 may be defined by a U-shaped cross-sectional portion 61 of stent 60. The U-shaped portion 61 defines a radially-inward-facing convex surface 61a and a radially-outward-facing concave surface 61b. The portion of stent 60 having channel 66 has a reduced cross-sectional area of lumen 64, as compared to the portion of stent 60 without channel 66. Channel 66 also may include a sloped surface 66a of wall 62, angled relative to a longitudinal axis of stent 60 toward, and at the end of, U-shaped portion 61 of channel 66. Channel 66 may be sized and shaped to receive tube 40 when EVAC device 20 and stent 60 are deployed in the body, which may provide an improved seal between target site 70 and GI tract 80. For example, channel 66 may seal tube 40 against the inner wall of GI tract 80 without creating any kinks or folds through which material and/or fluid may flow into target site 70. Stent 60 may be any material, including but not limited to Chitosan. Stent 60 also may include any covered, braided, or mesh stent, made of any suitable materials. (Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC®400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material). The cover may include, for example, any suitable polymers, plastics, or elastomers, and the braid or mesh may be any suitable plastics, metals, or alloys. Stent 60 may be flexible, bendable, and/or compressible to a reduced diameter and expandable to an increased diameter. In some instances, stent 60 may be formed of a self-expandable material (e.g., Nitinol) and may include a coating (e.g., Chitosan, silicone, urethane, Chronoflex, polytetrafluoroethylene (PTFE)) over at least a portion of the self-expandable material. For example, proximal and distal ends of stent 60 may include a material different from the material spanning the opening of target site 70. Additionally, or alternatively, the proximal and distal ends of stent 60 may be left uncoated to promote tissue growth for anti-migration.

Figure 2:
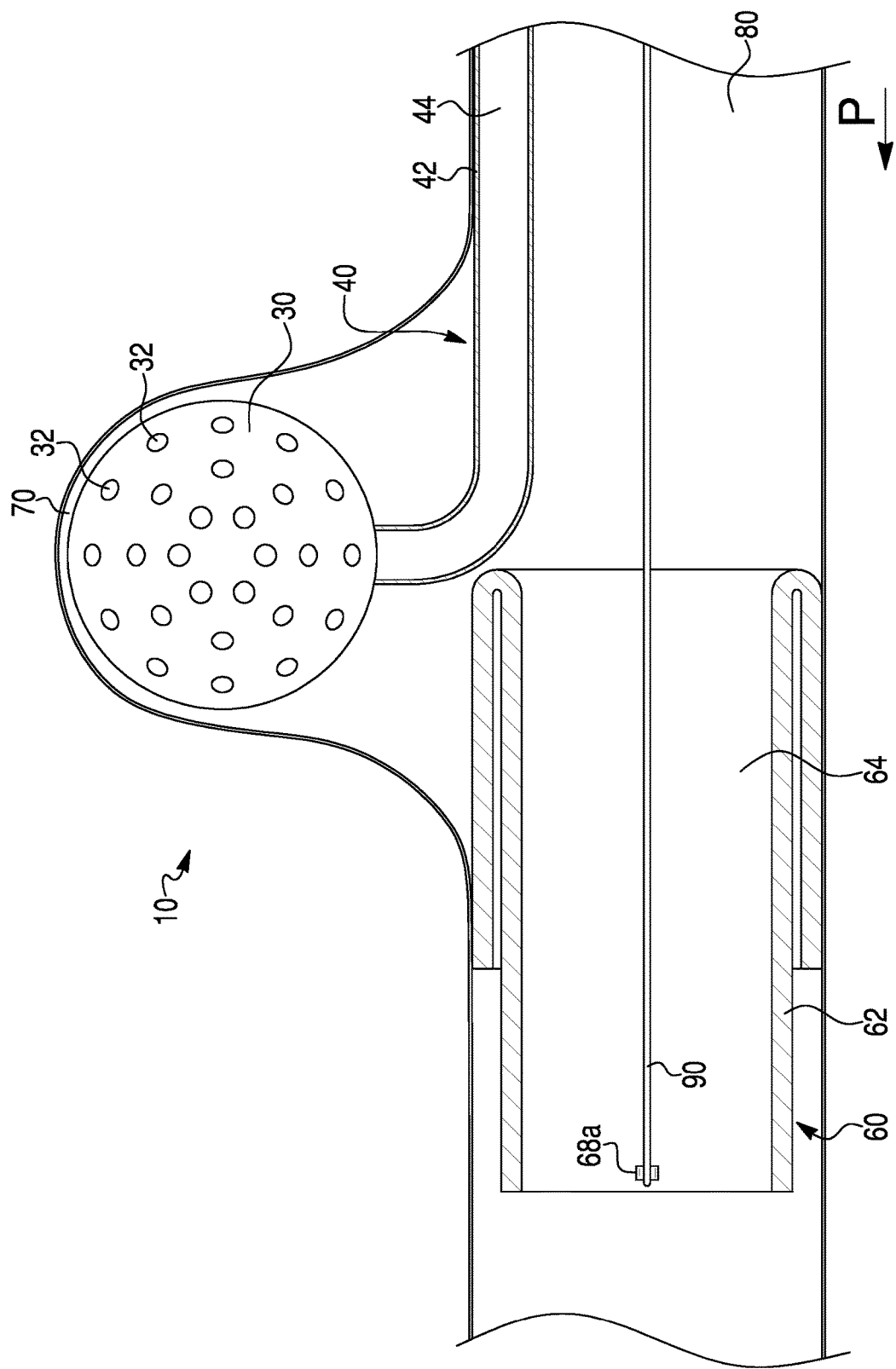
FIG. 2 is a view of the EVAC system of FIG. 1A having an inverted stent, according to an embodiment.

Stent 60 may also include a loop 68a (e.g., a hook, a suture, or other grasping mechanism) on an inner surface of lumen 64. Loop 68a may be connected to a portion of a covered braid of stent 60, for example. Loop 68a may be grasped by a tool 90 (FIG. 2) to invert or fold stent 60 in on itself. Tool 90 may be any medical instrument advanced to target site 70 and configured to engage loop 68a to move stent 60. Suitable instruments include graspers, forceps, and the like. Folding stent 60 in on itself may allow EVAC device 20 to be removed and/or replaced without removing stent 60, which may reduce procedure times and/or may reduce trauma. For example, FIG. 2 illustrates the proximal end of stent 60 being moved distally via loop 68a to move a proximal portion of stent 60 distally and invert that portion into a distal portion of stent 60.

Figure 3:
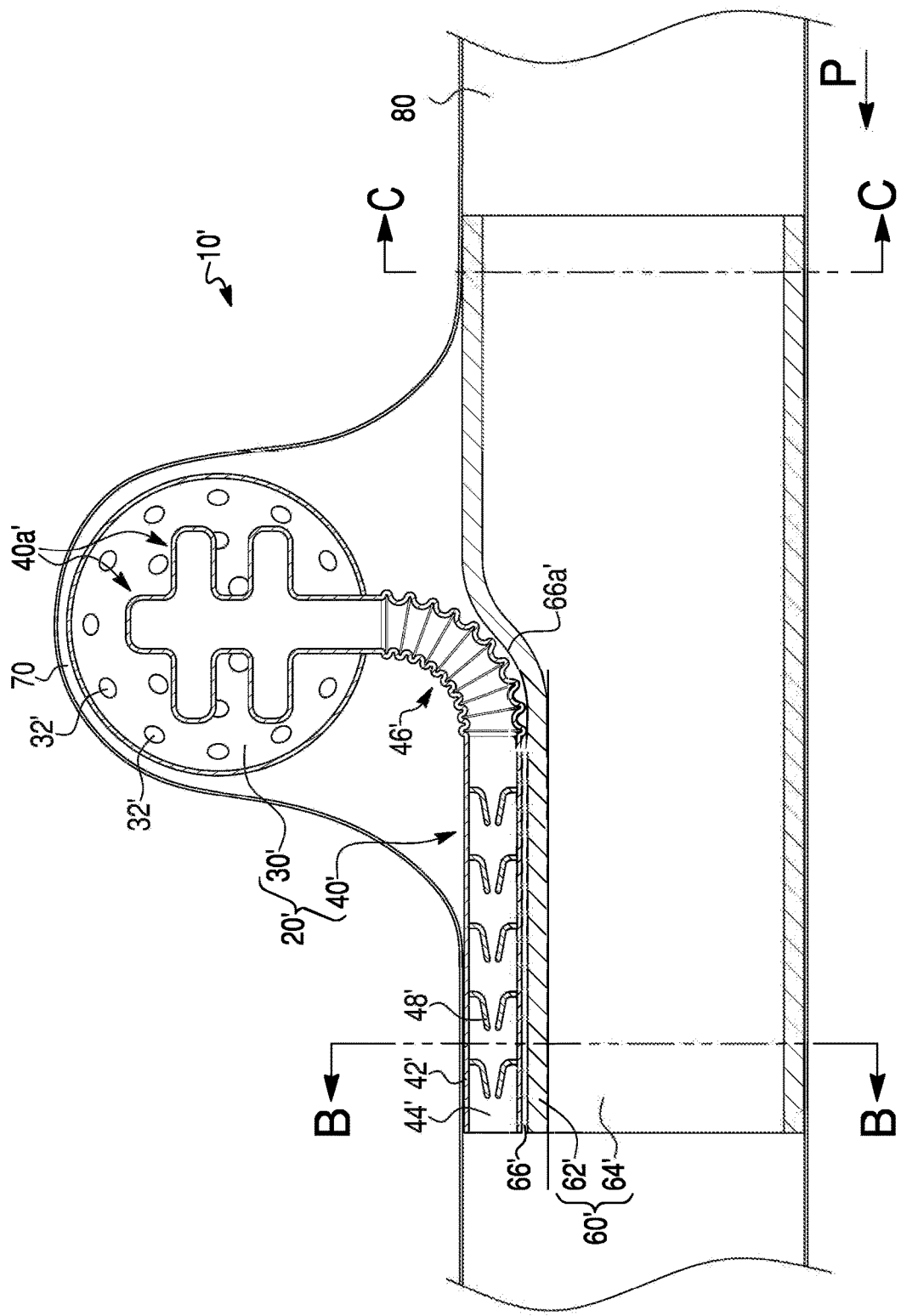
FIG. 3 is a cross-section of an EVAC system according to another embodiment.

Although stent 60 is shown with channel 66 extending from the proximal end of stent 60 in the distal direction, stent 60 may be deployed in the body such that channel 66 extends from the distal end of stent 60 in the proximal direction (see, e.g., FIG. 3).

A method of inserting system 10 will now be described. EVAC device 20 may be introduced via an orifice (e.g., a natural body orifice) and advanced to target site 70 using, e.g., a catheter. Sponge 30 may be placed at target site 70 and positioned such that tube 40 may extend in the proximal direction, e.g., in the direction opposite the direction indicated by arrow P in FIG. 2. In some examples, a fluid is introduced to expand sponge 30 from a reduced profile to an expanded profile. The fluid may be introduced by the catheter or an associated tool. Subsequently, stent 60 may be introduced via the orifice and advanced to target site 70 using, e.g., a stent delivery catheter and/or any other suitable medical stent delivery device known in the art. Stent 60 may be in an expanded configuration during deployment. Alternatively, stent 60 may be compressed, rolled, or folded on itself to reduce its profile and, once positioned adjacent target site 70, may be moved into the expanded configuration using, e.g., the stent delivery mechanism. After positioning stent 60 adjacent target site 70, stent 60 may be repositioned such that channel 66 is aligned with tube 40. For example, stent 60 may be rotated about its axis to align channel 66 and tube 40, and/or translated axially to align with target site 70, either before or after initial deployment. Subsequently, the catheter and any other associated tools may be removed from the body via the orifice.

In some examples, EVAC device 20 may be replaced after a predetermined period of time to insert a new, smaller sponge 30 (or a sponge having different mechanical and/or chemical properties) as the tissue at target site 70 heals. According to an example, tool 90 may be advanced from an orifice and may engage loop 68a. For example, tool 90 may engage loop 68a at the proximal end of stent 60 in FIG. 2. Tool 90 may be moved distally, folding stent 60 in on itself (inverting stent 60) to expose sponge 30 and tube 40. A catheter and/or a grasping tool may grasp EVAC device 20 and EVAC device 20 may be removed from the body. Alternatively, tube 40 may be pulled proximally, causing sponge 30 and tube 40 to move toward the insertion orifice. A different EVAC device 20 may then be advanced to target site 70 and sponge 30 may be placed at target site 70. Tube 40 may be positioned in GI tract 80 to extend proximally toward the insertion orifice. Tool 90 may then be pulled proximally, unfolding stent 60 to cover target site 70. As stent 60 is unfolded, tube 40 rests in channel 66, sealing sponge 30 and target site 70 from GI tract 80.

A system 10' according to another example is shown in FIG. 3. System 10' includes an EVAC device 20' and a stent 60'. System 10' may be inserted at target site 70 in GI tract 80.

EVAC device 20' may be similar to EVAC device 20. For example, EVAC device 20' may include a sponge 30' and a tube 40' extending from sponge 30'. Sponge 30' may include openings 32' connected to channels or pores, which may be in fluid connection to a proximal end of tube 40'. As described herein, the proximal end of tube 40' may includes branches 40a' which may be embedded in sponge 30' and which may increase the number and/or area of openings of tube 40' in fluid communication with sponge 30'. This increased number of openings may increase the fluid uptake by tube 40'. Tube 40' may be shorter than tube 40. For example, tube 40' may be approximately 200 mm in length. The length of tube 40' may depend on a length of stent 60'. For example, stent 60' may be approximately 40 mm to approximately 160 mm in length, and the length of tube 40' may be longer than stent 60'. In some instances, multiple stents 60' may be used in an overlapping fashion to maintain a position of device 20'. In this instance, tube 40' may be longer than the combined lengths of the overlapping stents 60'. The length of tube 40' may also be based on the anatomy of the patient, e.g., a distended stomach or a rectal reservoir. The length of tube 40' may be modified during the procedure by, e.g., cutting tube 40', to obtain a suitable length depending on the associated devices and/or anatomy.

When placed in the body, the distal end of tube 40' may extend distally, i.e., in a direction indicated by arrow P in FIG. 3, which may be a direction away from the insertion orifice. The extension direction of the distal end of tube 40' allows fluids to flow out of target site 70 and toward, e.g., the stomach and/or a natural exit orifice, such as the anus. Tube 40' may also contain a corrugated section 46' which may allow tube 40' to more easily bend adjacent a connection point between tube 40' and sponge 30' to allow tube 40' to extend in the proper direction in GI tract 80. Alternatively, or additionally, a thickness or a diameter of outer wall 42' of tube 40' may be reduced and/or a different material may be used in the vicinity of corrugated section 46' to assist in bending tube 40'.

Tube 40' may also include one or more one-way valves 48' which may close in the absence of fluid flow caused by the peristaltic action, and which may open in the presence of fluid flow caused by peristaltic action along the direction indicated by arrow P. For example, the peristaltic action in the direction of arrow P may cause sponge 30' to be squeezed by the walls of GI tract 80, including the walls at target site 70, which may cause a pressure at sponge 30', cause sponge 30' to uptake fluid from target site 70, and/or cause sponge 30' to release fluid into tube 40'. The fluid may travel from target site 70', through tube 40', and may be expelled at the distal end of tube 40' into GI tract 80. The pressure exerted by fluid expelled from sponge 30' during peristaltic action may be sufficient to open valves 48' and may allow the fluid to flow from sponge 30' toward the distal end of tube 40'. Valves 48' may prevent fluid, material, etc. taken up by sponge 30' at target site 70 from being drawn back into tube 40' and/or into target site 70 in the absence of the peristaltic action.

Stent 60' may be similar to stent 60 shown in FIGS. 1A and 2, and may include a lumen 64' defined by an outer wall 62'. Stent 60' may create a seal between target site 70 and GI tract 80. Unlike stent 60, a channel 66' of stent 60' extends from the distal end of stent 60' in the proximal direction, and terminates distally of the proximal end of stent 60'. While shown with channel 66', stent 60' may not include channel 66'. In this instance, stent 60' has sufficient flexibility to allow room for tube 40' between stent 60' and the wall of GI tract 80. Further, while not shown, stent 60' may include attachment or grasping elements which may assist during the insertion of stent 60' into the body and/or when folding (inverting) or unfolding stent 60'.

Figure 4A:
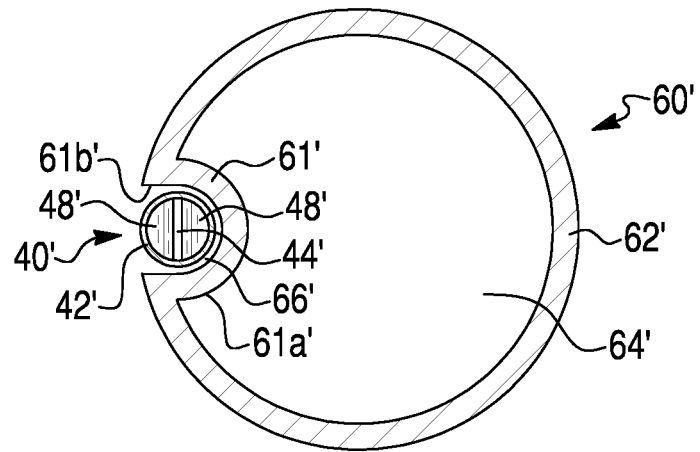
FIGS. 4A and 4B are cross-sections of the EVAC system of FIG. 3 along lines B-B and C-C, respectively, according to an embodiment.
Figure 4B:
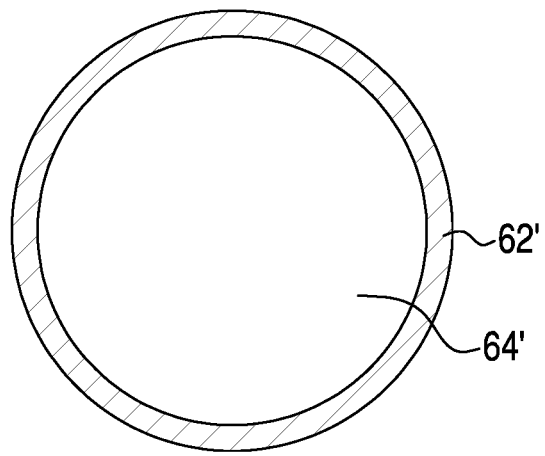

FIGS. 4A and 4B are cross-sectional views of system 10' taken along the lines B-B and C-C, respectively. Channel 66' may be defined by a U-shaped cross-sectional portion 61' of stent 60'. The U-shaped portion 61' defines a radially-inward-facing convex surface 61a' and a radially-outward-facing concave surface 61b'. The portion of stent 60' having channel 66' has a reduced cross-sectional area of lumen 64', as compared to the portion of stent 60' without channel 66'. Channel 66' also may include a sloped surface 66a' of wall 62' angled relative to a longitudinal axis of stent 60' toward, and at the end of, U-shaped portion 61' of channel 66'. Channel 66' may be sized and shaped to receive tube 40' when EVAC device 20' and stent 60' are deployed in the body, which may provide an improved seal between target site 70 and GI tract 80. For example, channel 66' may seal tube 40' against the inner wall of GI tract 80 without creating any kinks or folds through which material and/or fluid may flow into target site 70.

System 10' may be inserted into GI tract 80 at target 70 in a manner similar to that described with reference to system 10. For example, EVAC device 20' may be advanced to target site 70. Sponge 30' may be inserted into target site 70 and tube 40' may extend into GI tract 80 and extend distally of target site 70. Stent 60' may be inserted into GI tract 80 and deployed to seal target site 70 from GI tract 80.

Figure 5A:
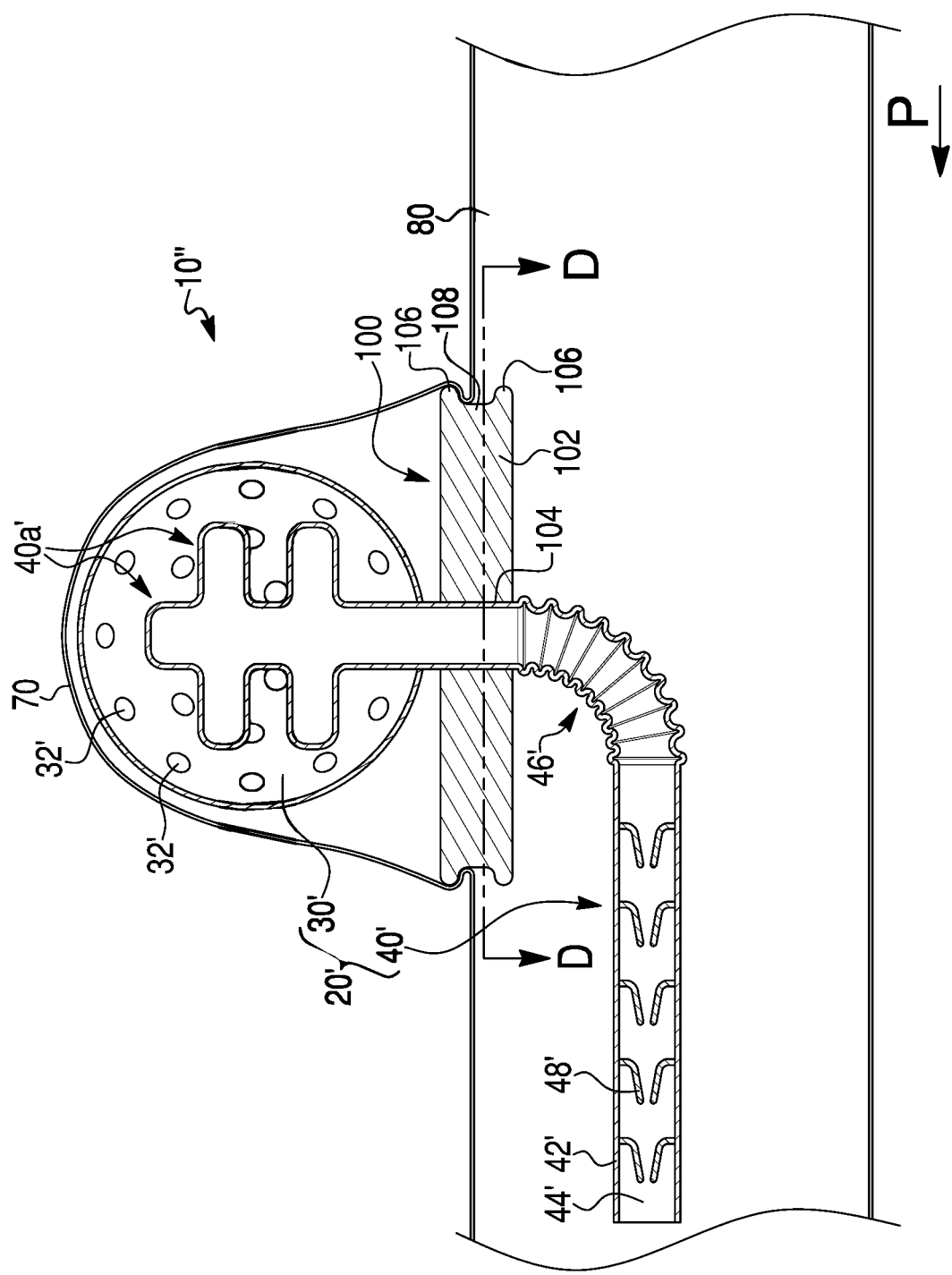
FIG. 5A is a cross-section of an EVAC system according to another embodiment.

A system 10" according to another example is shown in FIG. 5A. System 10" includes EVAC device 20' and a valve 100. Valve 100 may be biased to seal target site 70 from GI tract 80, yet able to attain an "open" configuration to release additional fluid from site 70 during peristaltic action. Similar to system 10' in FIG. 3, sponge 30' is disposed at target site 70 and tube 40' may extend from sponge 30' into GI tract 80. Valve 100 may be provided between sponge 30' in target site 70 and GI tract 80, which may prevent fluid from traveling from GI tact 80 into target site 70.

Valve 100 may include first rings 106 having an outer diameter greater than an outer diameter of a second ring 108. Second ring 108 may be disposed between first rings 106, such that first and second rings 106, 108 form a U-shaped (hourglass) outer side surface of valve 100. First and second rings 106, 108 may maintain a position of valve 100 between GI tract 80 and target site 70. For example, tissue of the outer wall of GI tract 80 may extend between first rings 106 (e.g., may be sandwiched between the outer lips of first rings 106) and may contact second ring 108 during deployment, such that one of first rings 106 is on an inner side of GI tract 80 and another of first rings 106 is on an outer side of GI tract 80. First rings 106 may contact the wall of GI tract 80 and may prevent valve 100 from moving during use. In other words, portions of valve 100 facing sponge 30' and portions of valve 100 facing GI tract 80 have a relatively larger diameter than a portion of valve 100 therebetween.

Valve 100 may be a solid, unitary structure, with surfaces facing sponge 30' and GI tract 80 being substantially planar and having any suitable shape. For example, valve 100 may be a unitary piece of material. Valve 100 also may be circular, polygonal, rectangular, or irregular based on a shape of the opening. In an example, a particular shape of valve 100 may be better suited for maintaining the position of valve 100 in the opening and sandwiched between tissue of GI tract 80. Valve 100 may also be larger than the opening between GI tract 80 and target tissue 70 to maintain the position of valve 100 during deployment.

Figure 5B:
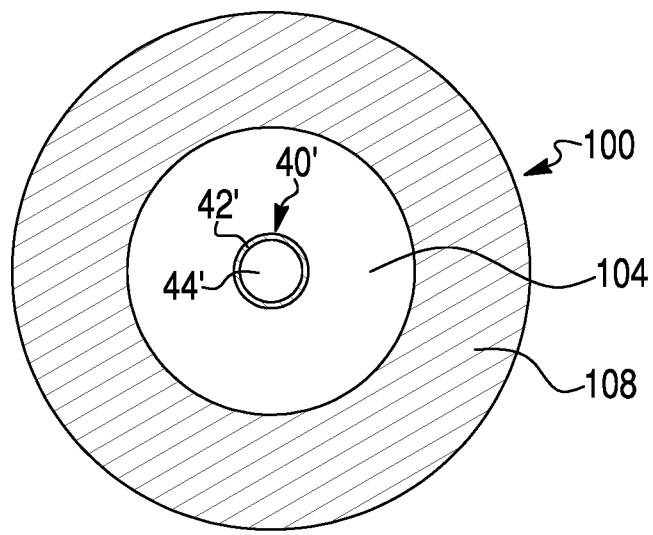
FIGS. 5B and 5C are cross-sections of a valve of the EVAC system of FIG. 5A along line D-D according to an embodiment.
Figure 5C:
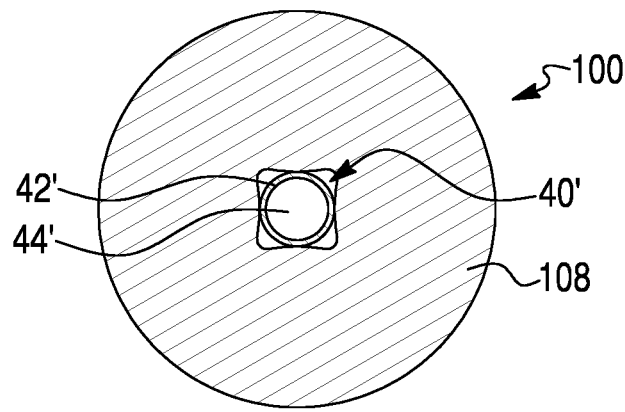

As shown in FIGS. 5B and 5C, which illustrate a cross section of valve 100 taken along the line D-D, valve 100 may include a central lumen 104 extending through rings 106, 108. Tube 40' may pass through lumen 104 to allow fluid and materials to pass from target site 70 to GI tract 80. FIG. 5B illustrates an open configuration of valve 100, and FIG. 5C illustrates a closed, or semi-closed, configuration of valve 100. When no peristaltic action is present, the wall of GI tract 80 may press on an outer surface of second ring 108, causing valve 100 to collapse on itself. In this example, portions of rings 106, 108 may collapse into lumen 104 due to a low durometer material forming those rings. In this collapsed configuration, valve 100 may approach and/or contact tube 40' about a circumference of tube 40', as shown in FIG. 5C. In this configuration, valve 100 prevents fluid and material from entering target site 70. While valve 100 has a generally circular outer surface in FIG. 5C, the tissue may cause valve 100 to have any shape in the collapsed configuration, such as an irregular shape, based on the various forces of the tissue of GI tract 80 on valve 100.

When a peristaltic action occurs, target site 70 may be squeezed, increasing pressure within target site 70. As discussed herein, peristaltic action may force material and fluid from sponge 30' through tube 40'. In addition, the increased pressure on fluid and material in target site 70 may overcome the force of the walls of GI tract 80 of valve 100, and may permit valve 100 to attain an expanded configuration as shown in FIG. 5B. Expanding lumen 104 permits material and fluid to flow from target site 70 into GI tract 80. As the peristaltic action ends, valve 100 may collapse about tube 40' to close lumen 104. In this manner, the capacity of system 10" to dispel additional material and fluid from target site 70 with each peristaltic action wave increases. Valve 100 may be any material suitable for medical use including, but not limited to, rubber, polymers, or the like.

A method of inserting system 10" will now be described. EVAC device 20' may be inserted in a manner similar to that discussed relative to systems 10 and 10'. Once sponge 30' is positioned at target site 70', valve 100 may be advanced to target site 70' using, e.g., a catheter and/or an associated delivery tool. Tube 40' may be placed through lumen 104 of valve 100 and valve 100 may be placed between target site 70 and GI tract 80. The wall of GI tract 80 may be maneuvered to fit into the U-shaped space defined by first and second rings 106, 108. The catheter and/or any associated tool may be subsequently removed from the body via the orifice. Alternatively, tube 40' may extend through lumen 104 of valve 100 before insertion. Thus, EVAC device 20' and valve 100 may be advanced to target site 70 at a same time. Sponge 30' may be placed at target site 70. The walls of GI tract 80 may be placed into the U-shaped space and between first rings 106 of valve 100.

It will be understood that any EVAC device, including a sponge or mesh device and a tube configured to remove fluid or other material from a target site, may be used alone or in combination with one or more of the sealing devices described herein.

While different medical systems have been described, it will be understood that the particular arrangements of elements in these EVAC systems are not limited. Moreover, a size, a shape, and/or the materials of the EVAC systems are not limited. As described herein, there are included patches or sealing devices for sealing a sponge and a target site from a body lumen. For example, performing various medical procedures may be improved by ensuring a proper seal between the target site and any debris or materials in a body lumen. This seal may prevent these materials (e.g., fecal matter) from entering the target site and passing into another body organ through, e.g., a post-surgical leak, and causing infections or other medical issues.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical system, comprising:
    a porous body configured to be positioned at a target site within a subject;
    a tube including a wall defining a tube lumen, wherein the tube is connected to the porous body at a first end of the tube; and
    a sealing device configured to seal the target site from a body lumen, the sealing device including an outer wall surrounding a sealing device lumen within the sealing device;
    wherein, when the sealing device seals the target site from the body lumen, the tube is configured to extend from the target site, into the body lumen, completely exterior of the sealing device lumen, wherein the sealing device includes a channel defined by a radially-outward-facing concave surface of the sealing device, wherein the channel includes a sloped surface angled relative to a longitudinal axis of the sealing device toward and at an end of the channel, and wherein the sloped surface of the channel contacts the tube along a length of a curved surface of the tube.

2. The medical system of claim 1, wherein the sealing device is a stent, and wherein the stent is configured to contact (1) a sidewall of the body lumen and (2) the tube, when the tube and the stent are implanted.

3. The medical system of claim 2, wherein a proximal portion of the sealing device lumen has a smaller cross-sectional area than a distal portion of the sealing device lumen.

4. The medical system of claim 1, wherein a grasping device extends from the outer wall into the sealing device lumen.

5. The medical system of claim 4, wherein the grasping device is a loop configured to be grasped by another medical device to move an end of the sealing device into the sealing device lumen or out of the sealing device lumen.

6. The medical system of claim 1, wherein the tube extends within the channel.

7. The medical system of claim 6, wherein the channel extends distally from a first end of the channel between a proximal end of the sealing device and a distal end of the sealing device to a second end of the channel proximate the distal end of the sealing device.

8. The medical system of claim 6, wherein the channel is configured to be aligned with the tube when the tube and the sealing device are implanted to seal the tube against a sidewall of the body lumen.

9. The medical system of claim 1, wherein the first end of the tube includes a plurality of branches embedded in the porous body.

10. The medical system of claim 1, wherein the tube includes a plurality of corrugations, and wherein the tube is configured to bend via the plurality of corrugations.

11. The medical system of claim 1, wherein a second end of the tube is configured to be open to the body lumen, wherein the tube includes a plurality of one-way valves, and wherein the plurality of one-way valves are configured to allow fluid to pass from the target site into the body lumen, and inhibit fluid from passing from the body lumen into the target site.

12. A medical device, comprising:
   a porous body configured to be positioned at a target site;
   a tube including a tube lumen extending from a first end of the tube to a second end of the tube and connected to the porous body at the first end of the tube, wherein the tube includes at least one one-way valve configured to pass fluid from the first end of the tube to the second end of the tube and inhibit fluid from passing from the second end of the tube to the first end of the tube, wherein the tube lumen is fluidly connected to the porous body at the first end of the tube;
   a sealing device configured to seal the target site from a body lumen, wherein an entirety of the tube is configured to extend radially outward of a wall of the sealing device; and
   a channel defined by the wall of the sealing device, wherein the channel includes a sloped surface angled relative to a longitudinal axis of the sealing device and at an end of the channel, and wherein the sloped surface contacts and extends along a length of a curved surface of the tube.

13. The medical device of claim 12, wherein the first end of the tube includes a plurality of branches embedded with the porous body, wherein the tube lumen extends through each branch of the plurality of branches, and wherein each branch of the plurality of branches includes an opening fluidly connecting the tube lumen with the porous body.

14. The medical device of claim 12, wherein the tube includes a plurality of corrugations, and wherein the tube is configured to bend via the plurality of corrugations.

15. The medical device of claim 12, wherein the channel is configured to seal the tube against a sidewall of the body lumen when the tube and the sealing device are implanted.

16. The medical device of claim 12, wherein the second end of the tube is configured to be within the body lumen.

17. A method of removing fluid from a target site adjacent a gastrointestinal tract, the method comprising:
   deploying a porous body within the target site, wherein the target site is accessed through an opening in a wall in the gastrointestinal tract, and a tube extends from the porous body into the gastrointestinal tract;
   deploying a stent within the gastrointestinal tract, wherein the stent includes a channel defined by a radially-outward-facing concave surface of the stent, and wherein the channel includes a sloped surface angled relative to a longitudinal axis of the stent and at an end of the channel; and
   rotating the stent to align the channel, including the sloped surface, with the tube after deploying the stent to seal the target site from the gastrointestinal tract.

18. The method of claim 17, further comprising:
   moving an end of the stent into a stent lumen;
   removing the porous body from the gastrointestinal tract;
   deploying a second porous body within the target site; and
   moving the end of the stent from the stent lumen to seal the target site from the gastrointestinal tract.

19. The method of claim 18, wherein moving the end of the stent into the stent lumen exposes the porous body and the target site to the gastrointestinal tract.

\* \* \* \* \*